United States Patent [19]

Colon et al.

[11] Patent Number: 5,241,072

[45] Date of Patent: Aug. 31, 1993

[54] OLIGOSACCHARIDE OXAZOLINES, OLIGOSACCHARIDE CONJUGATES AND METHODS OF PREPARATION THEREOF

[75] Inventors: Marcelo Colon, Gurabo, P.R.; Jeffrey T. Davis, Watertown, Mass.; James R. Rasmussen, Cambridge, Mass.; Marianne Borowski, Boston; Barbara Y. Wan, Tewksbury, Mass.; Shirish Hirani, Boston, Mass.

[73] Assignee: Genzyme Corporation

[21] Appl. No.: 529,343

[22] Filed: May 25, 1990

[51] Int. Cl.$^5$ .................................. C07D 498/02
[52] U.S. Cl. .................................. 548/218; 536/179; 536/124; 536/17.3; 530/333
[58] Field of Search .............. 548/218; 536/17.9, 124

[56] References Cited

U.S. PATENT DOCUMENTS 4,681,936 7/1987 Pfaff et al. .................... 536/124
4,785,084 11/1988 Warren et al. ................ 548/218
4,830,852 5/1989 Marburg et al. .

FOREIGN PATENT DOCUMENTS 8800951 2/1988 PCT Int'l Appl. .

OTHER PUBLICATIONS

Yamazaki et al. Chem Abstr vol. 95 entry 204347q (1981).
Thiem et al, Chem. Abstr. vol. 91 entry 4188f (1980).
Gros et al. Chem Abstr vol. 77 entry 75384b (1972).
Srivastava Carbonydrate Res. vol. 103 pp. 286-292 (1982).
Allerhand et al. (1984) J. Am. Chem. Soc. 106 pp. 2412-2420.
Aplin et al. (1981) CRC Critical Reviews in Biochemistry 10 pp. 259-306.
Ashwell et al. (1974) Adv. Enzymol. Relat. Areas Mol. Biol. 41 pp. 99-128.
Baenziger (1984) The Plasma Proteins, vol. IV, pp. 271-315.
Berger et al. (1982) Experientia 38 pp. 1129-1162.

Colon et al. (1991) Tetrahedron Letters 32 pp. 4447-4450.
Dorland et al. (1981) J. Biol. Chem. 256 pp. 7708-7711.
Gros et al. (1972) Carbohyd. Res. 23 pp. 148-151.
Gunther et al. (1990) Angew. Chem. Int. Ed. Engl. 29 pp. 1050-1051.
Hauglund (1989) Handbook of Fluorescent Probes and Research Chemicals, Molecular Probes, Inc., Eugene, Ore., pp. 53-55.
Hirani et al. (1987) Anal. Bioch. 162 pp. 485-492.
Ji (1983) Methods in Enzymology 91, Part 1, pp. 580-609.
Kornfeld and Kornfeld (1985) Ann. Rev. Biochem. 54 pp. 631-664.
Laemmli (1970) Nature 227 pp. 680-685.
Lee et al. (1982) The Glycoconjugates, vol. IV, pp. 57-83.

(List continued on next page.)

*Primary Examiner*—Donald G. Daus

[57] ABSTRACT

This invention relates to a method of producing peracetyloxazolines from peracetyl saccharides. The method involves reacting the starting material, a peracetyl saccharide, with a reagent combination, to directly produce the peracetyl oxazoline. This method may be used for the activation of oligosaccharides, wherein an oligosaccharide containing a reducing GlcNAc terminus is activated by the formation of an orazoline at the terminal GlcNAc, and then coupled with a bifunctional spacer to provide an oligosaccharide-spacer conjugate. The activated oligosaccharide-spacer conjugate is then coupled to a protein, such as granulocyte colony stimulating factor or γ-interferon, providing a neoglycoprotein conjugate. The invention provides a method for forming neoglycoprotein conjugates which may improve biological and physiochemical properties of the protein. For example, serum lifetime or efficiency of drug delivery of the peptide to a target organ or cell may be improved.

6 Claims, 5 Drawing Sheets

OTHER PUBLICATIONS

Lee et al. (1976) Biochemistry 15 pp. 3956–3963.
Magnusson et al. (1989) J. Org. Chem. 55 pp. 3932–3946.
Marsh et al. (1977) J. Biol. Chem. 252 pp. 7678–7684.
Marshall (1978) Trends Biochem. Sci. 3 pp. 79–83.
Matta et al. (1973) Carbohyd. Res. 26 pp. 215–218.
Nakabayashi et al. (1986) Carbohyd. Res. 150 pp. C7–C10.
Nakabayashi et al. (1988) Carbohyd. Res. 174 pp. 279–289.
Rademacher et al. (1988) Ann. Rev. Biochem. 57 pp. B785–B838.
Reddy et al. (1990) Biochem. 29 pp. 2482–2487.
Snider (1984) Biology of Carbohydrates 2 pp. 164–198.
Stowell (1980) Advances in Carbohydrate Chemistry and Biochemistry 37 pp. 225–281.
Thiem et al. (1980) Chem. Ber. 113 pp. 3075–3085.
Thurl et al. (1986) Hoppe Seyler's Biol. Chem. 367 pp. 191–197.
Warren et al. (1977) Carbohyd. Res. 53 pp. 67–84.
Warren et al. (1980) Carbohyd. Res. 92 pp. 85–101.
Warren et al. (1984) Carbohyd. Res. 126 pp. 61–80.
Wilson (1978) J. Biol. Chem. 253 pp. 2070–2072.
Yamashita et al. (1982) J. Biol. Chem. 257 pp. 12809–12814.
Yamashita et al. (1983) J. Biol. Chem. 258 pp. 3099–3106.
Yamazaki et al. (1981) Can. J. Chem. 59 pp. 2247–2252.

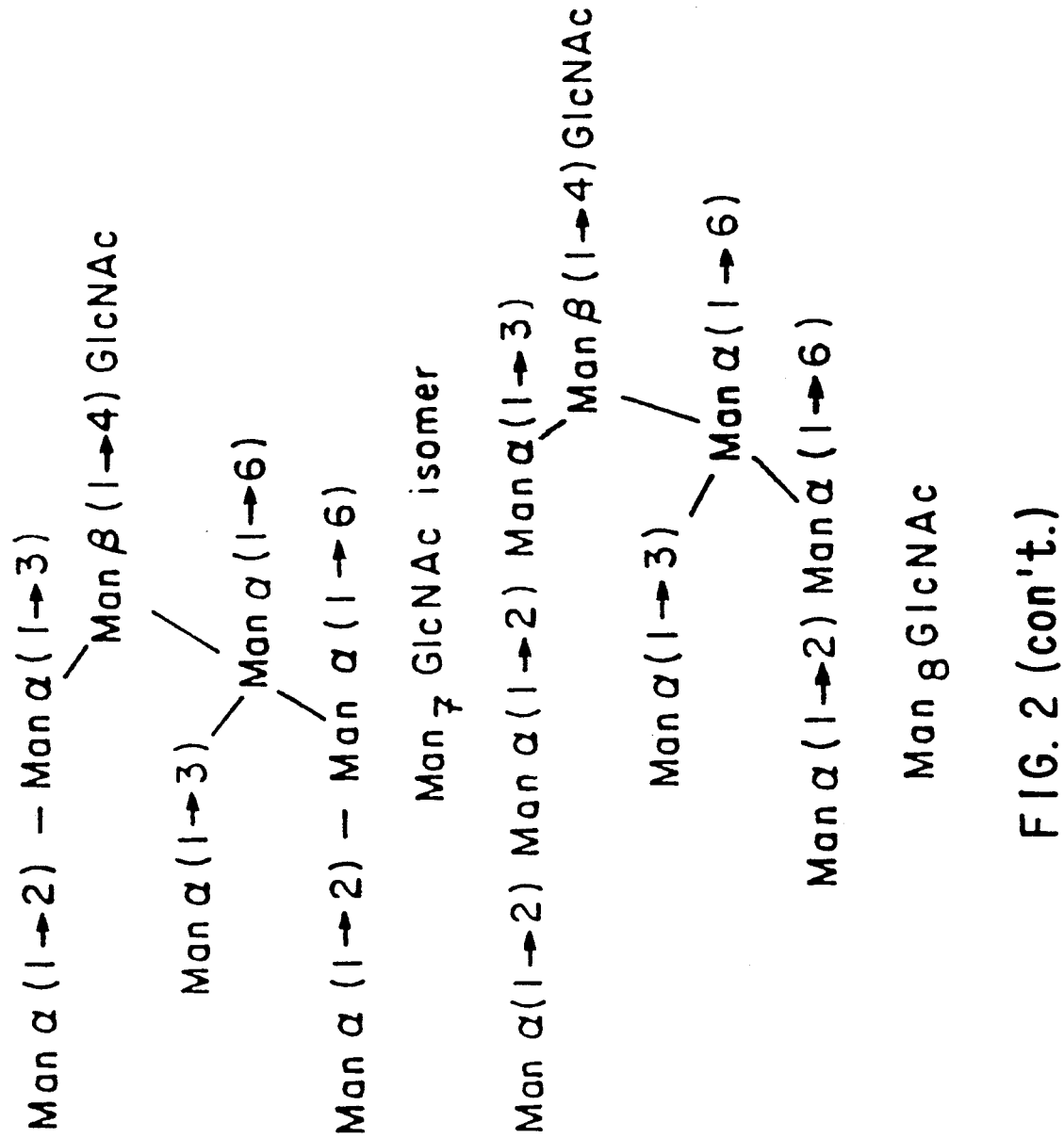
FIG. 2 (con't.)

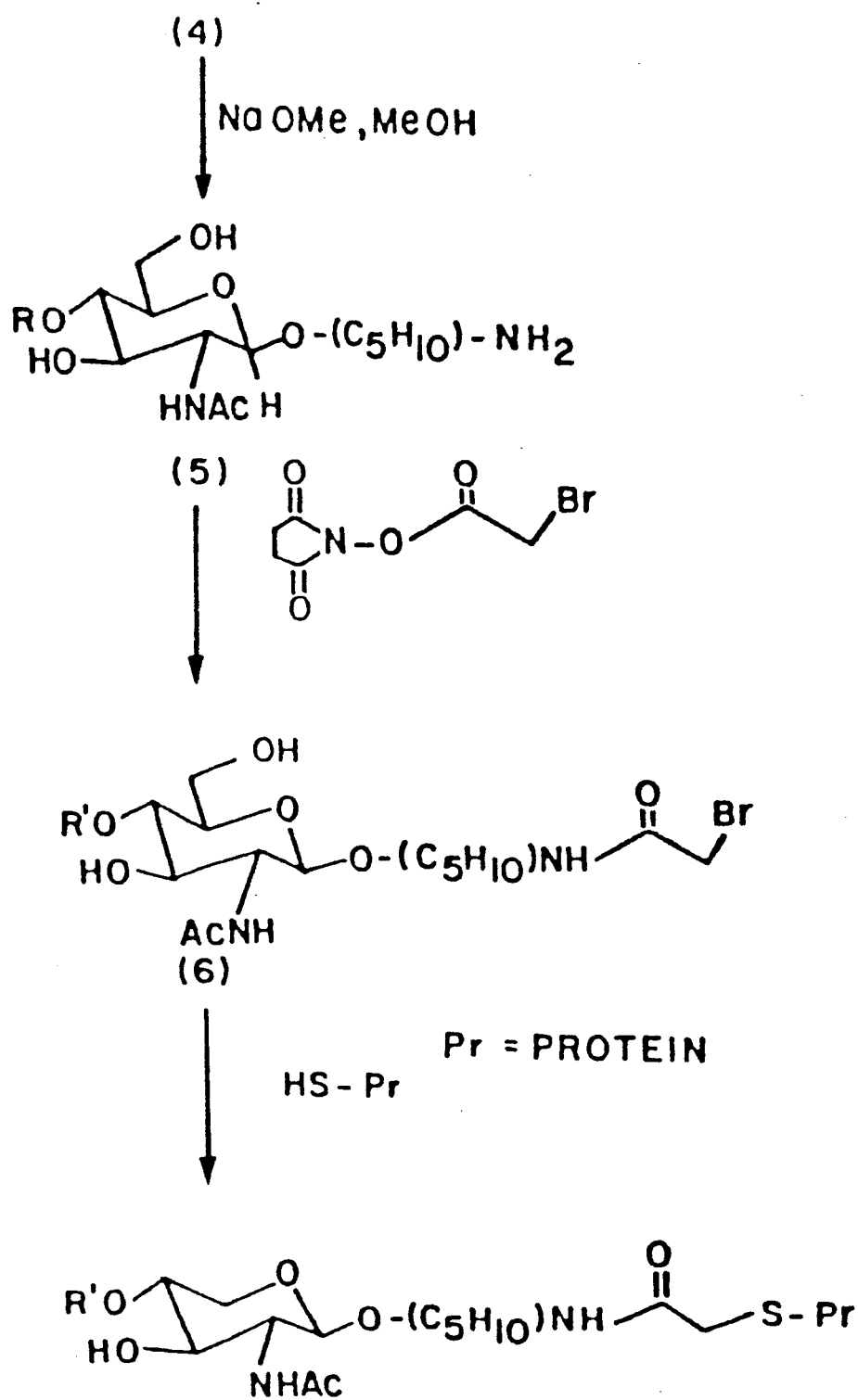
FIG. 3 (con't.)

OLIGOSACCHARIDE OXAZOLINES, OLIGOSACCHARIDE CONJUGATES AND METHODS OF PREPARATION THEREOF

TECHNICAL FIELD

The invention relates to methods for the preparation of oligosaccharide oxazolines and to oligosaccharide conjugates and the preparation thereof.

BACKGROUND ART

Glycoproteins, covalent conjugates of carbohydrates and proteins, are essential in maintaining and regulating intracellular and extracellular biological activities in a living organism. The external surface of the cellular plasma membrane is enriched with glycoproteins which function as cell surface receptors for growth factors, hormones and toxins. In addition, glycoproteins secreted into extracellular fluids exist as growth factors, hormones, enzymes and antibodies. The effect of the carbohydrate moieties on the biological activity of glycoproteins is a subject of continuing studies. It has been shown that carbohydrate moieties play a vital role in regulating the structure and function of a glycoprotein. The carbohydrate moieties may mediate the cellular uptake of the protein, protect the protein from denaturation and proteolytic degradation, or modulate physical properties of the protein such as viscosity, stability, circulatory lifetime and binding capacity (Experientia (1982) 38, pp. 1129-1162; and Ann. Rev. Biochem. (1988) 57, pp. 785-838). Recent studies also demonstrated the ability of the oligosaccharide moieties of glycoproteins to reduce self-association of the proteins (Biochem. (1990) 29, pp. 2482-2487).

Glycosylation is a biologically important modification of the covalent structure of a protein. There are two categories of glycosylation recognized in most eukaryotic systems: O-linked glycans are attached to proteins via an α-glycosidic linkage to either serine or threonine, while the more frequent N-linked glycans are covalently attached via β-glycosidic bond to an asparagine moiety. Protein N-glycosylation occurs co-translationally in the endoplasmic reticulum with the oligosaccharide $Glc_3Man_9GlcNAc_2$ being transferred en bloc from the lipid carrier dolichol diphosphate to an asparagine residue contained in the peptide sequence of Asn-X-Ser(Thr). Subsequent processing of the nascent glycoprotein in the Golgi by a battery of glycosidases and glycosyltransferases gives rise to a myriad of possible structures for the mature N-linked glycan. Many literature reviews of the structure, function and biosynthesis of N-linked glycans have been recently published (Baenzinger in The Plasma Proteins (1984) IV pp. 271-315; Snider in Biology of Carbohydrates (1984) 2, pp. 164-198; and Kornfeld and Kornfeld in Ann. Rev. Biochem. (1985) 54 pp. 631-664).

A necessary step in obtaining information concerning N-glycan structure, function and biosynthesis is the development of synthetic methodology for the preparation of specific asparagine N-linked glycans, as well as the oligosaccharide dolichol diphosphate lipid intermediate and other carbohydrate derivatives.

Syntheses of all these glycosides is dependent on the chemical "activation" of the terminal GlcNAc moiety of the glycan. One successful glycosyl activation strategy involves the acid-catalyzed formation of an oxazoline intermediate from peracetylated oligosaccharides. For instance, Warren et al. in International Patent Application PCT/U587/01832 describe the synthesis of a high-mannose oligosaccharide asparagine derivative, from an oxazoline derivative and Warren et al. (Carbohydr. Res. (1984) 126 pp. 61-80) also describe the use of an oxazoline to prepare the dolichol diphosphate lipid intermediate.

The synthetic methodology utilized by Warren et al. in the preparation of asparagine-linked high-mannose oligosaccharide derivatives was based on a three-step protocol: (1) addition of azide to the oxazoline intermediate so as to obtain the β-linked azido derivative, (2) reduction of the β-azide to a β-1-amino glycoside and (3) coupling of the glycosylamine to the appropriately protected aspartate moiety. The general synthesis of Asn-linked oligosaccharides is thus ultimately dependent on a mild and efficient method for oxazoline generation. The Asn-linked oligosaccharides are of importance because they may be incorporated into N-linked glycopeptides by condensation of various peptides to the glycosylated asparagine amino-acid moiety. These N-linked glycopeptides have potential use, not only as glycosidase substrate analogues, but also as model systems for studying the structure and dynamics of N-linked glycoproteins.

Peracetyl oxazolines of mono- or disaccharides are traditionally prepared via chloroacetolysis (acetyl chloride in concentrated HCl) of the corresponding peracetyl saccharide. Warren et al. (Carbohydr. Res. (1977) 53 pp. 67-84, (1980) 92 pp. 85-101, and (1984) 126 pp. 61-80) describe the preparation of the peracetylated oxazolines of various saccharides. A severe problem associated with the chloroacetolysis procedure is the susceptibility for cleavage of any acid-labile glycosidic bonds. For instance any α-D (1→6) glycosidic linkages in the particular oligosaccharide and the βD(1→4) linkages between the two N-acetylglucosamines (GlcNAc) of the oligosaccharide's chitobiose core are particularly prone to acid-catalyzed glycosidic cleavage. The relatively harsh conditions of the chloroacetolysis reaction are therefore not amenable to many structurally complex oligosaccharides.

The direct formation of a peracetyl oxazoline from the peracetate using a Lewis acid as catalyst is an alternative approach to the chloroacetolysis method. Matta et al. in Carbohydr. Res. 1973) 26 pp. 215-218 describe the formation of an oxazoline from the β-D-anomer of peracetyl saccharides using anhydrous ferric chloride. Ferric chloride does not, however, catalyze formation of the oxazoline from the predominant α-D-anomer of the peracetyl saccharide. Because of its inability to promote oxazoline formation from the major anomer the ferric chloride method is of limited applicability.

Scrivastava describes a method, using ferric chloride, for oxazoline generation from the α-D-anomer of peracetyl glucosamine (Carbohydr. Res. (1982) 103 pp. 286-292). When this method was applied to peracetyl oligosaccharides the predominance of side reactions led to low yields of desired product. Nakabayashi et al., in Carbohydr. Res., (1986) 150 C7-C10 and Warren et al., in International Patent Application PCT/U587/01832 describe an alternative Lewis-Acid catalyzed procedure for oxazoline generation. This method is designed to circumvent the two aforementioned problems of poor anomeric selectivity and low overall yields of oxazoline. Using one equivalent of the Lewis acid trimethylsilyl trifluoromethanesulfonate these authors formed a peracetyl oxazoline from a heptasaccharide peracetate isomer (Man$_5$GlcNAc$_2$). Nakabayashi et al. claimed that the heptasaccharide oxazoline was accessible from either the α or β anomer, and they also reported that no glycosidic bond cleavage was detected.

Activated oligosaccharide derivatives may be reacted with proteins to form oligosaccharide-protein conjugates (neoglycoproteins). Because oligosaccharides have a wide spectrum of biological activity, the formation of neoglycoproteins is valuable for improving the biological and physiochemical activity of proteins. Marburg et al. reported a method of preparing oligosaccharide conjugates wherein oligosaccharides are activated by the addition of carbonyldiimidazole or nitrophenyl chloroformate and then reacted with a spacer group with a pendant electrophilic group followed by reaction with a nucleophilic group on a protein (U.S. Pat. No. 4,830,852 (1989)). Some neoglycoproteins have improved thermal stability and increased stability towards proteases and denaturants. For example, after incubation at 60° C. for 10 min, lactosylated E. coli L-asparaginase retains 63% of its activity, whereas the native enzyme retains only 19%. The same modification is also reported to stabilize the asparaginase towards proteolytic digestion. Lactosylated asparaginase retains 50% of its activity after a 60 min incubation with subtilisin, whereas the native asparaginase is completely deactivated after only 20 min incubation (J. Biol. Chem. (1977) 252 pp. 7678.) In addition, neoglycoproteins often have longer circulatory lifetimes. For example, dextran-amylase conjugates have a circulatory lifetime which is 4.5 times longer than the unmodified enzyme (Trends Biochem. Sci. (1978) 3 pp. 79.)

Another interesting aspect of neoglycoproteins is their potential in efficient drug delivery, especially in targeting therapeutic proteins to particular cells or organelles. Endocytosis of glycoproteins is often mediated by the interaction of cell-surface receptors and the glycoprotein carbohydrate components. The attachment of the appropriate carbohydrate components could result in the delivery of neoglycoproteins to specific tissues or organs of the body. For example glycoproteins with terminal galactose are selectively removed from circulation by hepatocytes (Adv. Enzymol. Relat. Areas Mol. Biol. (1978) 41 pp. 99-128). In another example, by attaching lactose to the bovine pancreatic RNAse A dimer, the uptake of the protein was shifted from the kidney to the liver, where galactosyl receptors are located (J. Biol. Chem. (1978) 253, pp. 2070-2072). It has also been shown that the binding affinity of mannosylated bovine serum albumin to the mannose-receptors on rabbit alveolar macrophages increases dramatically, even with a small increase in the number of mannose attached (Biochemistry, (1988) 15 pp. 3956.) Thus, neoglycoproteins hold great therapeutic potential, especially in the treatment of diseases caused by enzyme deficiencies.

There have been numerous methods reported in the literature for the covalent coupling of carbohydrates to proteins (Advances in Carbohydrate Chemistry and Biochemistry (1980) 37 pp. 225-281; CRC Critical Reviews in Biochemistry (1981) pp. 259-306; Glycoconjugates (1982) IV pp. 57-83). For example, p-aminophenyl glycosides of the oligosaccharide may be diazotized and allowed to react with lysyl, tyrosyl and histidyl residues of the protein. Alternatively, the p-aminophenyl glycoside may be converted to an isothiocyanate and attached to amino functional groups on the protein. Another method of neoglycoprotein production involves amidation between a carboxy group and an amine facilitated by dicyclohexylcarbodiimide (DCC), 3-(3-dimethylaminopropyl)-1-ethylcarbodiimide (DAEC) or mixed anhydrides. The carboxy component may be the protein's side-chain carboxy groups or aldonic acids generated by oxidation of the terminal oligosaccharide residue. The amino component may be aminoglycosides or lysines of the protein. Hydrazido-oligosaccharides derivatives may be converted by treatment with nitrous acid into acyl azides, which are highly reactive towards lysine residues of proteins.

Direct coupling of carbohydrates to proteins may also be achieved by reductive amination. In this procedure, the reducing terminus of the oligosaccharide is allowed to react with the amino groups of the protein to form a Schiff base; the Schiff base is subsequently reduced with sodium cyanoborohydride, providing a hydrolytically stable amine linkage between carbohydrate and protein. In general, there is a current need for efficient and specific methods which allow coupling of proteins and oligosaccharides.

SUMMARY OF THE INVENTION

The present invention relates, in one embodiment, to a novel method for the direct preparation of peracetyl oxazolines from peracetyl oligosaccharides. In another embodiment, the invention also relates to the use of peracetyl oxazoline derivatives of oligosaccharides as efficient glycosylation agents for the chemical synthesis of glycoconjugates (i.e. O-glycosides, glycolipids, glycopeptides, etc.). Using the methods described in the invention, an oligosaccharide, containing a reducing GlcNAc terminus, may be activated by the formation of an oxazoline at the terminal GlcNAc, and then coupled to a bifunctional spacer. In accordance with an embodiment of the invention, the oligosaccharide may then be coupled to a therapeutically useful protein, such as granulocyte colony stimulating factor or γ-interferon, providing a neoglycoprotein conjugate. The formation of a neoglycoprotein conjugate of a therapeutically valuable protein may enhance serum lifetime of the protein, or may improve the efficiency of drug delivery of the protein to a target organ or cell.

BRIEF DESCRIPTION OF FIGURES

The foregoing features of the invention will be more readily understood by reference to the following detailed description taken with the accompanying figures, in which.

DETAILED DESCRIPTION OF SPECIFIC EMBODIMENTS

A. Preparation of Oligosaccharides

Figure 1:
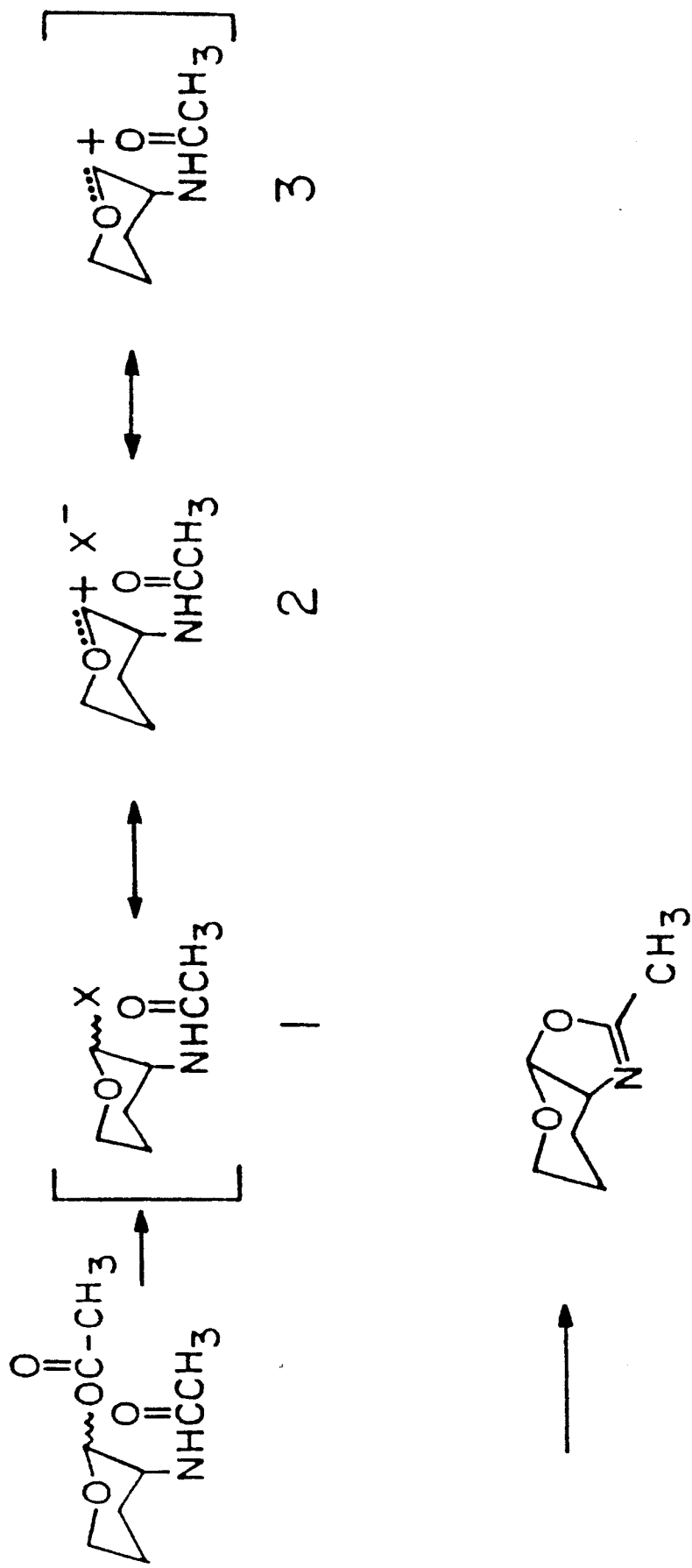
FIG. 1 illustrates possible reaction intermediates in the generation of oxazoline product from peracetyl saccharides using reagent combinations described herein.
Figure 2:
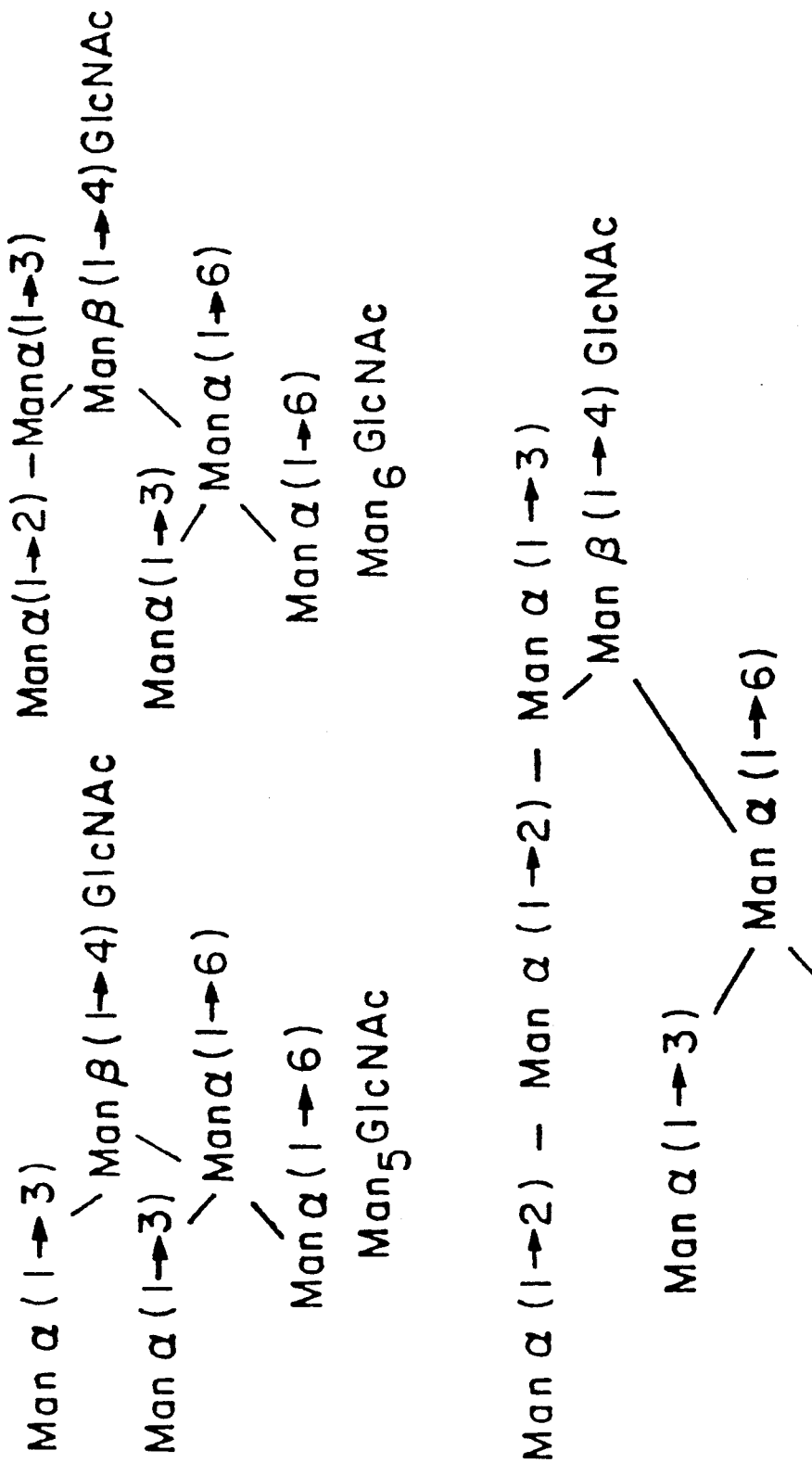
FIG. 2 illustrates the structure of the high mannose type oligosaccharides, Man$_5$GlcNAc, Man$_6$GlcNAc, the two isomers of Man$_7$GlcNAc, and Man$_8$GlcNAc.

The oligosaccharide derivatives used in embodiments of this invention are derived from any oligosaccharide containing a 2-acetamido-2-deoxyglucopyranose(GlcNAc) at the reducing terminus of the oligosaccharide.

Suitable oligosaccharides include, but are not limited to, high mannose type oligosaccharides, hybrid-type oligosaccharides and complex type oligosaccharides. Preferred sources of the oligosaccharides include oligosaccharides from glycoproteins and glycopeptides which are enzymatically released by the action of endoglycosidases such as endo-H and amidases such as N-Glycanase; or chemically released, for example, by hydrazinolysis. Examples of such glycoproteins include high mannose glycoproteins such as 7S globulin (J. Biol. Chem. (1981) 256 pp. 7708), ribonuclease B (Hoppe Seyler's Biol. Chem. (1986) 367 pp. 191), and ovalbumin (J. Am. Chem. Soc. (1984) 106 pp. 2412.) The structure of high mannose type oligosaccharides are illustrated in FIG. s. Other examples include complex-type glycoproteins such as α-1-acid glycoprotein, transferrin and fetuin (Anal. Bioch. (1987) 162 pp. 485), as well as hen ovomucoid (J. Biol. Chem. (1982) 257 pp. 12809) and turkey ovomucoid (J. Biol. Chem. (1983) 258 pp. 3099.) The complex-type oligosaccharides may or may not be sialylated. However, in the chemical modification step, the desialylated complex oligosaccharide is preferred. The terminal sialic acid may be added in a later step using sialyl transferase.

B. Preparation of Oligosaccharide Oxazolines

Attempts by scientists at Genzyme Corporation to form an oxazoline from a high-mannose nonasaccharide peracetate ($Man_8GlcNAc$) using the Nakabayashi procedure (op. cit.) met with only marginal success. While the minor β-D-anomer (ca 10%) rapidly formed the desired oxazoline, the predominant α-D-anomer was extremely sluggish in forming product using the Nakabayashi procedure. Prolonged reaction times and elevated temperatures, while giving increased yields of oxazoline also led to significant glycosidic bond cleavage, severely compromising the purity of the final product. These unsatisfactory results with the nonasaccharide peracetate have prompted the development of an alternative method for oxazoline preparation. The embodiment described below of the present invention is better suited for the preparation of peracetyl oxazolines from structurally complex and acid-labile oligosaccharide peracetates.

In general, the invention features, in one embodiment, a method for the preparation of oxazolines from peracetyl saccharides containing an N-acetylglucosaminyl residue as the reducing terminus of the saccharide. The conditions utilized in this method are sufficient to catalyze formation of the oxazoline from either the α or β anomer of the peracetyl saccharide, yet mild enough so that no concommitant glycosidic bond cleavage is detected. The method involves reacting a peracetyl saccharide with a particular combination of reactive compounds capable of catalyzing the formation of an intermediate acetoxonium ion so as to subsequently produce the peracetyl oxazoline. The critical aspect of this embodiment is the judicious combination of two reagents, which when used in tandem, catalyze oxazoline formation. Treatment of the starting peracetyl saccharide with either reagent alone, however, results in no reaction. Neither reagent, when alone or when combined with the other reagent, promotes any deleterious side-reactions of the starting peracetyl saccharide. This contrasts to the behavior of the more reactive Lewis acid, trifluoromethanesulfonic acid, which while leading to oxazoline formation, gives significant glycosidic cleavage when particular oligosaccharides are utilized.

In accordance with an embodiment of this invention, a peracetyl oxazoline may be prepared from a peracetyl saccharide which may be derived from either a naturally occurring or a synthetic mono-, di- or oligosaccharide containing an N-acetyl-glucosamine at the reducing terminus of the saccharide. The oligosaccharide obtained from natural sources may be produced by digestion of an N-linked glycoprotein or glycopeptide, with either (1) an endoglycosidase such as endo-H or (2) an amidase such as N-glycanase or they may be obtained by (3) hydrazinolysis of the N-linked glycoprotein or glycopeptide.

If a peracetyl oligosaccharide is derived from natural sources it may be either a high-mannose, a complex or a hybrid oligosaccharide. The oligosaccharide will typically contain one to twelve residues of neutral hexoses, with at least one residue, the reducing terminal residue, being an N-acetylhexosamine. The oligosaccharide may also contain fucose or sialic acid residues. In addition, the reducing N-acetylglucosamine residue may be present in either the α or the β configuration.

While the preferred protecting group for the hydroxyl functionalities of the oligosaccharide is the acetyl residue other protecting groups are amenable for oxazoline preparation. For instance pertrichloroacetyl, pertrifluoroacetyl or perbenzoyl oligosaccharides may also be used to generate reactive oligosaccharide oxazoline derivatives. In some cases it may be preferable to prepare oxazoline from pertrichloroacetyl or pertrifluoroacetyl oligosaccharides as these two protecting groups are more easily deprotected by base hydrolysis than the peracetyl oligosaccharides. Perbenzoyl oligosaccharides are, by contrast, hydrolytically more stable than their peracetate analogs.

The peracetyl saccharide is reacted with a combination of reagents capable of generating the formation of intermediates 1, 2, or 3 (FIG. 1). The initial acetolysis catalyzed by the reagent combination may lead to the formation of an intermediate glycosyl halide 1, an intimate ion-pair 2, or a glycosyl cation 3 (FIG. 1). In the process of this invention, all three intermediates may undergo neighboring-group addition of the C-2 N-acetamido group to preferentially or exclusively yield the peracetyl oxazoline. Glycosyl halide 1 may undergo an intramolecular $S_N2$ reaction or similarly heterolysis of the C-1 halogen bond may lead to the intimate ion pair 2 or the glycosyl cation 3, both of which are stabilized immediately by intramolecular attack of the C-2 acetamide group. In each case, the final product is peracetyl oxazoline. Reagent combinations capable of generating the desired peracetyl oxazoline include, but are not limited to, mixtures of boron trifluoride-etherate ($BF_3$-$OEt_2$) and bromotrimethylsilane (TMS-Br), chlorotrimethylsilane (TMS-Cl), or iodotrimethylsilane (TMS-I). The combination of $BF_3$-$OEt_2$ and TMS-Br is preferred. One fifth equivalent of the peracetyl saccharide is reacted with a ratio of one equivalent of $BF_3$-$OEt_2$ to one to ten equivalents of TMS-Cl or TMS-Br, with a ratio of one equivalent of $BF_3$-$OEt_2$ to one equivalent of TMS-Cl or TMS-Br being preferred. In addition, from one to ten equivalents of an acid scavenger per equivalent of $BF_3$-$OEt_2$ may be added to the reaction mixture so as to accelerate oxazoline product formation and protect against any acid-catalyzed decomposition of the oxazoline product. For example 2,4,6-collidine, pyridine, triethylamine, or other tertiary amines may be used as the acid scavenger, with 2,4,6-collidine being preferred.

The foregoing method is carried out in an anhydrous organic solvent with dichloroethane being preferred. The reaction conditions include temperatures of 0° C. to 50° C., and times of 2 to 24 hours with a preferred temperature being 20° C. and a preferred time being 2 hours. The reaction may be monitored by thin layer chromatography (tlc) on glass plates coated with analytical grade silica gel using 10:1 (v/v) chloroform-methanol or 10:1 (v/v) ethyl acetate-methanol as the solvent system.

After the reaction is judged to be complete, the product peracetyl oxazoline may be isolated and purified by silica gel column chromatography. In one embodiment, the reaction mixture is washed with water, the organic layer is dried over $Na_2SO_4$, concentrated, and the crude high-mannose oligosaccharide oxazoline is purified by column chromatography on Kieselgel 60 silica (230–400 mesh) with elution effected by 40:1 chloroform-methanol. The yield is approximately 95% based on the peracetyl saccharide.

The peracetyl oxazolines prepared according to this invention may be used as glycosyl donors in the chemical synthesis of oligosaccharides, glycolipids, glycopeptides, glycoproteins, and other useful β-D-glycosides. In the presence of the proper reagent combination any of the aforementioned intermediates (1, 2, or 3) may react to form oxazoline. The reagent combination may be a 1:1 mixture of bromotrimethylsilane or chlorotrimethylsilane, and boron trifluoride etherate. In addition, one equivalent of an acid scavenger such as 2,4,6-collidine, for example, may be used to accelerate oxazoline generation and also to prevent acid catalyzed decomposition of both the oxazoline and the starting saccharide. The present invention provides a method greatly superior to the method of Nakabayashi et al. (op. cit.) which was found to be unsuitable for the generation of oxazoline from the predominant alpha anomers of Man$_n$GlcNAc (where n is an integer in the range from and including 5 through 8) oligosaccharides isolated from the soybean 7S globulin. Thus when a 90:10 a:b mixture of the peracetates of Man$_n$GlcNAc were treated with trimethylsilyl trifluoromethanesulfonate according to the Nakabayashi et al. protocol, only the minor β-isomer formed oxazoline while the c-anomer resisted reaction. Prolonged reaction times or elevated temperatures led to significant glycosidic bond cleavage and generation of unacceptable amounts of side products. Optimum conditions for oxazoline formation were determined using 2-acetamido 1,3,4,6-tetra-O-acetyl-2-deoxy-α-D-glucopyranose as a model study. Tables 1 and 2 summarize the results. Table 1 shows data describing the reaction of 2-acetamido-1,3,4,6-tetra-O-acetyl-2-deoxy-α-D-glucopyranose with various combinations of the reagents TMS-bromide and BF$_3$ etherate Table 2 shows data describing the reaction of 2-acetamido-1,3,4,6-tetra-O-acetyl-2-deoxy-α-D-glucopyranose with a 1:1 ratio of TMS-bromide and BF$_3$-OEt$_2$ in the presence of various amounts of the acid scavenger 2,4,6-collidine.

TABLE 1

Preparation of oxazoline from 2-acetamido-1,3,4,6-tetra-O-acetyl-2-deoxy-α-D-glucopyranose using various reagent combinations*.

| Entry | Reagent Combination[a] | Acid Scavenger[b] | Time | Yield |
|---|---|---|---|---|
| 1 | BF$_3$-OEt$_2$ | 0 | 24 hrs | 0% |
| 2 | TMSBr | 0 | 24 hrs | 0% |
| 3 | BF$_3$-OEt$_2$ + TMSBr | 0 | 16 hrs | 70% |
| 4 | BF$_3$-OEt$_2$ + TMSBr | 1 | 24 hrs | 95% |

*50 mg of starting material was dissolved in 2 ml of anhydrous dichloroethane and stirred with the corresponding reagent combinations at room temperature. The reaction was monitored by t.l.c. (10:1, v/v chloroform/methanol). When the reaction was complete, it was washed with water, dried with Na$_2$SO$_4$, concentrated in vacuo, applied to a column of silica gel (Kieselgel 10; 230–400 mesh) and eluted with 40:1 (v/v) chloroform/methanol. The product was identified by $^1$H NMR.
[a]1 molar equivalent of the reagent combination to one molar equivalent of starting material was used.
[b]Equivalents of 2,4,6-collidine per equivalent of starting material.

TABLE 2

Preparation of oxazoline from 2-acetamido-1,3,4,6-tetra-O-acetyl-2-deoxy-α-D-glucopyranose using a 1:1 combination of TMS-bromide and BF$_3$-OEt$_3$* and various equivalents of acid scavenger.

| Entry | Equivalents[a] | Acid Scavenger[b] | Time | Yield |
|---|---|---|---|---|
| 1 | 1 | 0 | 24 hrs | 55% |
| 2 | 1 | 1 | 24 hrs | 90% |
| 3 | 2 | 2 | 15 hrs | 97% |
| 4 | 5 | 5 | 7 hrs | 95% |
| 5 | 10 | 10 | 5 hrs | 96% |

*50 mg of starting material was dissolved in 2 ml of anhydrous dichloroethane and stirred with the corresponding reagents at room temperature. The reaction was monitored by t.l.c. (10:1, v/v chloroform/methanol). When the reaction was complete, it was washed with water, dried with Na$_2$SO$_4$, concentrated in vacuo, applied to a column of silica gel (Kieselgel 10; 230–400 mesh) and eluted with 40:1 (v/v) chloroform/methanol. The product was identified by $^1$H NMR.
[a]mmol of the 1:1 TMS-bromide-boron trifluoride etherate combination per mmol of starting material.
[b]equivalents of 2,4,6-collidine per equivalents of the 1:1 combination of TMS-bromide and boron trifluoride etherate.

The present invention provides methods superior to currently available methods for preparing peracetyl oxazolines from structurally complex oligosaccharides. Due to the mild reaction conditions, peracetyl oligosaccharides containing acid-labile linkages may be used in the process of this invention. Unlike most previously reported methods, the invention can work equally well with either the alpha or the beta anomer of the starting peracetyl saccharide.

C. Preparation of Oligosaccharides-Spacer Conjugates

The next step is the acid-catalyzed addition of a bifunctional spacer to the oligosaccharide-oxazoline. The reaction yields specifically a β-glycosidic bond between the terminal GlcNAc of the oligosaccharide and the bifunctional spacer. The oligosaccharide-spacer conjugate has the general formula: Os-A-B-C where Os is the oligosaccharide with a terminal GlcNAc, A is β-O- or β-NH-C=O, B is a spacer and C is either a cysteine-reactive group such as:

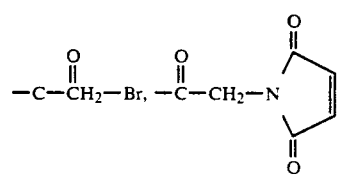

or a lysine reactive group such as:

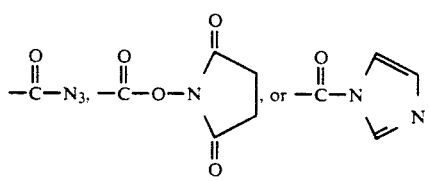 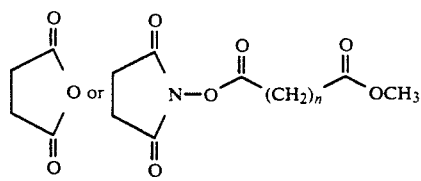

The bifunctional spacer may then be represented by A'-B-C where A' is a functional group which is reactive towards the oxazoline, and B and C are as described above. There are numerous examples of bifunctional spacers reported in the literature (for example, those cited in Methods in Enzymology 91, Part 1, pp. 581–609; and Handbook of Fluorescent Probes and Research Chemicals, Molecular Probes Inc. (1989)). A preferred embodiment of the bifunctional spacer may be represented by HO-$(CH_2)_n$-X-Y-$(CH_2)_n$-Z wherein:

n is an integer in the range from and including 0 through 10;

X is C=O, C=NH, $(CH_2)_n$, or N-R and R is H, or $CH_3$;

Y is C=O, C=NH, $(CH_2)_n$, N-R, S; and

Z is N-R or $(CH_2)_n$

The bifunctional spacer may have the electrophilic group, for example —C—$CH_2$—Br, already attached, or it may be masked by protecting groups such as HNC(O)$CF_3$, which may be deprotected and further functionalized after the addition to the oligosaccharide-oxazoline. In a typical example, N-trifluoroacetyl-5-amino-pentanol, a bifunctional spacer, is allowed to react with oligosaccharide-oxazoline in the presence of p-toluenesulfonic acid. The reaction proceeds at ambient temperature, under a nitrogen atmosphere for 16 hr. The O- and N- protecting groups on the resultant oligosaccharide-spacer conjugate are removed by treatment with NaOMe/MeOH in ambient temp for 4–24 hr. The oligosaccharide-spacer conjugate so obtained is further functionalized with the addition of an electrophilic moiety. Suitable reagents for such transformation include agents such as:

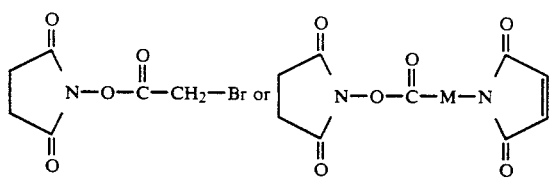

where M is an aromatic ring or $(CH_2)_n$, where n is an integer from and including 1 through 5.

Alternatively the oligosaccharide-oxazoline is treated with trimethylsilyl-azide in the presence of a Lewis acid such as tin(IV) chloride. The resultant oligosaccharideazide is subsequently reduced to give the 1-amino-oligosaccharide. The reduction may be accomplished by hydride transfer, for example using lithium aluminum hydride, or by catalytic hydrogenation, for example using palladium(O) on charcoal or platinum oxide (Adams catalyst) as catalysts. The 1-amino-oligosaccharide so obtained may be coupled with bifunctional spacers such as:

D. Preparation of the Protein

The proteins being utilized for the synthesis of oligosaccharide-protein conjugates using the methods of this invention include, but are not limited to, proteins of therapeutic value such as serum albumin, γ-interferon, granulocyte-colony stimulating factor(G-CSF), superoxide dismutase and interleukin-2. In addition to conjugates formed with proteins, conjugates may be formed similarly with peptides and polypeptides. The use of the term "protein" in the disclosure and claims herein, in this context, is introduced to include peptides and polypeptides.

The proteins utilized in embodiments of this invention include those possessing nucleophilic groups such as cysteine, lysine, or histidine. The cysteines may be present either as a free cysteine or as a disulfide. Preferably, these sulfhydryl groups are not required for the biological activities of the protein being modified. These sulfhydryl groups may be sterically or chemically accessible, for example, Cys-34 on bovine serum albumin, which may react readily with the activated oligosaccharide in the conjugation step. Others may resist chemical modification due to steric hindrance or disulfide formation. Nucleophilic groups that are sterically inaccessible, for example, Cys-17 on granulocyte-colony stimulating factor (G-CSF), may be exposed for reaction by adding denaturants such as urea or guanidine, or by adding detergents like tween-20 and sodium dodecylsulfate. Disulfides on proteins, for example, those on murine γ-interferon, can be reductively cleaved by reagents such as dithiothreitol, 2-mercaptoethanol or sodium borohydride. The reductively exposed sulfhydryls may then be reacted with the activated oligosaccharides.

E. Conjugation of Protein with Activated Oligosaccharide to provide Neoglycoprotein Neoglycoproteins obtained in accordance with an embodiment of this invention may be represented by the formula: Os-A-B-C-Nu-Pr wherein:

Os is the oligosaccharide with the terminal GlcNAc;

A is β-O- or β-NH-C=O;

B is the spacer group defined in part A;

C is the product of the reaction between the electrophilic group on the oligosaccharide with the nucleophilic group on the protein having the formula:

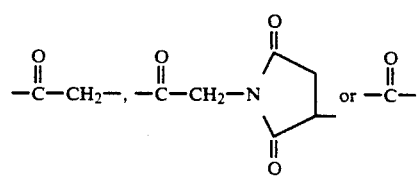

Nu is the nucleophilic group on the protein; and

Pr is the protein.

The protein-oligosaccharide conjugate is formed by reacting the suitably prepared protein with the activated oligosaccharide derivatives, preferably in molar ratios of 1:1 to 1:30 respectively, in aqueous buffered solution, at a pH of 7 to 9. The reaction is usually performed under a nitrogen atmosphere, at temperatures from 0° to 37° C., for a time period ranging from one to twenty-four hours. Examples of such reaction include:

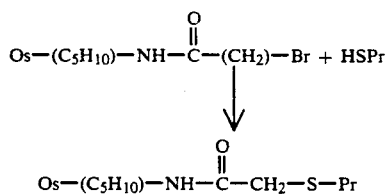

wherein an oligosaccharide activated with N-bromoacetyl-aminopentyl group is allowed to react with a protein that has been suitably prepared, or

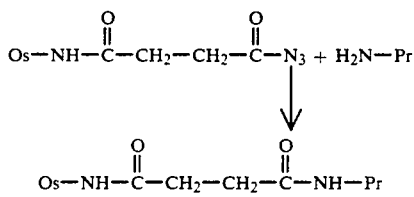

wherein an oligosaccharide activated with an acylazide group is allowed to react with a protein that has been suitably prepared. The excess activated oligosaccharide derivative may be removed by standard methods such as dialysis and gel filtration.

F. Purification of the oligosaccharide-Protein Conjugate

The protein-oligosaccharide conjugate may be purified by affinity lectin chromatography. For example, Concanavalin A is a lectin which has high specificity for high-mannose type oligosaccharide. In a typical example of purification using Con A lectin, the mixture of unreacted native protein and high-mannose oligosaccharide-protein conjugate is applied onto a Con A lectin column which is equilibrated at a temperature of 4° to 25° C. with the appropriate buffer. The unreacted native protein is collected in the void volume of the lectin column while the neoglycoprotein is eluted with 0.5M methyl mannoside. The excess methyl mannoside may be removed by dialysis, by gel filtration or by ultrafiltration through an Amicon system. High performance liquid chromatography (HPLC) may also be used to purify neoglycoprotein from unreacted native protein. Glycosylation of proteins usually leads to increased hydrophilicity, which leads to a shorter retention time on a reverse-phase HPLC column. Ion exchange HPLC may also be applied towards the purification of proteins modified with ionic oligosaccharides, such as those containing sialic acids.

G. Analysis is of the Oligosaccharide-Protein Conjugate

The oligosaccharide-protein conjugate can be analyzed by SDS-polyacrylamide gel electrophoresis according to the procedure of Laemmli (Nature (1970) 227 pp. 680-685). The oligosaccharide-protein conjugate has a higher molecular weight than the native protein. The difference in molecular weight of the oligosaccharide-protein conjugate and the native protein is the weight of the oligosaccharide covalently bound to the protein. Lectin blots using a lectin that has high affinity for the particular oligosaccharide, for example, concanavalin A lectin for high mannose type oligosaccharide, further prove the association of the oligosaccharide with the protein. Analysis of the reaction mixture, obtained from the conjugation step in part C by HPLC, may also provide information on the percentage of protein labelled with oligosaccharide. The oligosaccharide-protein conjugate may also be analyzed by high-resolution mass spectroscopy.

To locate the site of conjugation on the protein, a radiolabeled oligosaccharide derivative may be used in the conjugation step described in part C. For example, the oligosaccharide-amine is allowed to react with the N-hydroxysuccinimidyl-[$^{14}$C]-bromoacetate. The [$^{14}$C]-labeled activated oligosaccharide is conjugated to the protein. The purified radiolabelled oligosaccharide-protein conjugate is subjected to PICO TAGTM T-M ↑ amino acid analysis (Waters Assoc.). The dried radiolabeled oligosaccharide-protein conjugate is hydrolyzed to its free amino acids with 6N HCl for 20 to 24 hr. at 105° to 112° C. The amino acids are derivatized with phenylisothiocyanate for 20 min at 20° to 25° C. and the derivatives analyzed by reverse-phase HPLC. The presence of radiolabelled carboxymethylcysteine proves that the cysteine residue of the protein is covalently modified with the oligosaccharide. Furthermore, the radiolabeled oligosaccharide-protein conjugate may be fragmented by treatment with cyanogen bromide, or by digestion with proteases such as trypsin, chymotrypsin, endoproteinase C, ficin, and carboxypeptidases. The peptide fragments thus obtained may be analyzed by HPLC methods and those fragments containing the radiolabeled cysteine are collected. The amino acid sequence of these fragments may be determined by standard procedures. A comparison of the amino acid sequence of these fragments with those of the native protein may yield information on the exact location of the labeled cysteine residue.

In accordance with the invention, formation of neoglycoprotein conjugates from oligosaccharides and therapeutically valuable proteins can provide proteins with improved biological and physiochemical properties. The neoglycoprotein conjugates may have reduced tendencies toward aggregation and higher solubilities in aqueous medium. For example, the high mannose oligosaccharide-modified G-CSF has a shorter retention time on a reverse-phase HPLC column, which suggests higher hydrophilicity. The addition of an oligosaccharide moiety to a therapeutically useful protein may also enhance its stability towards denaturation and proteolytic degradation. The neoglycloproteins may also be used for improved drug delivery. Due to the specific interaction between oligosaccharides and cell surface receptors, neoglycoproteins may be delivered to specific tissues of the body. For example, high mannose oligosaccharide-modified proteins may be targeted specifically to macrophages where cell surface receptors for high mannose oligosaccharides are located. In addition, complex-type oligosaccharide-modified proteins may be targeted specifically to hepatocytes.

EXAMPLES

Example 1

Preparation of the Oxazoline Derivative of 2-acetamido-1,3,4,6-tetraacetyl-2-deoxy-α-D-glucopyranose (GlcNAc peracetete)

In an oven-dried flask, under a nitrogen atmosphere 2-acetamido-1,3,4,6-tetraacetyl-2-deoxy-α-D-glucopyranose (50 mg, 0.128 mmol) was dissolved in 2 ml of anhydrous dichloroethane (Aldrich). Addition of bromotrimethylsilane (Aldrich, 88.5 μ, 0.64 1 mmol), boron trifluoride etherate (Aldrich, 79 μl, 0.64 mmol) was made via syringe. The mixture was stirred at room temperature for 6 hr and then diluted with methylene chloride (10 ml). The reaction mixture was washed with sat. $NaHCO_3$, $H_2O$ and sat. NaCl solution. The organic layer was dried ($Na_2SO_4$) and concentrated in vacuo. The crude material was purified by flash chromatography on silica gel (Kieselgel 10: 230–400 mesh) using 40:1 (v/v) chloroform/methanol as eluant to give 48.5 mg (97%) of the desired oxazoline as a colorless oil. The oxazol be ideally characterized by the following: Rf=0.50, silica gel 60F254 (Merck), $CH_3Cl_3$—MeOH (10:1); 400 MHZ $^1H$ NMR ($CDCl_3$) ppm 5.98(d) 1 H, 5.28(s) 1 H, 4.95(d) 1 H, 4.17 (m) 3 H, 3.60(m) 1 H, 2.12(m) 12 H.

EXAMPLE 2

Preparation of the oxazoline Derivative of Chitobiose (GlcNAc β-1→4GlCNAc) Peracetate In an oven-dried flask under $N_2$ atmosphere chitobiose (GlcNAc β-1→4GlcNAc) (Sigma, 135 mg, 0.2 mmol) was dissolved in 4 ml of anhydrous 1,2-dichloroethane (Aldrich). Addition of bromotrimethylsilane (Aldrich, 124 μl, 0.9 mmol), boron trifluoride etherate (Aldrich, 111 μl, 0.9 mmol), and 2,4,6-Collidine (Aldrich, 120 μl, 0.9 mmol) was made via syringe. The mixture was allowed to stir at 20° C. overnight. Methylene chloride (15 ml) was added to the reaction mixture and the reaction mixture was washed with sat. $NaHCO_3$ solution, $H_2O$ and sat. NaCl solution. The organic layer was dried ($Na_2SO_4$) and concentrated in vacuo. The crude material was purifed by flash chromatography (2:1 EtOAc/hexane; 10:1 $CHCl_3$/MeOH) on silica gel (230–400 mesh, EM Science) to give the desired product as an amber oil (70 mg, 57%). The chitobiose oxazoline product will be ideally characterized by the following: Rf=0.55, silica gel 60F254 (Merck), $CHCl_3$—MeOH (10:1); 400 MHZ $^1H$ NMR ($CDl_3$) ppm 5.86 (m) 2 H, 5.20(t) 1 H, 5.80(t) 1 H, 4.72(d) 1 H, 4.32(m) 2 H, 4.14(m) 3 H, 3.92(m) 1 H, 3.75(m) 1 H, 3.50(d) 1 H, 3.42(m) 1 H, 2.20–1.95(m) 18 H, 1.69(s) 3 H.

EXAMPLE 3

Process for the Preparation of the Oxazoline from a Man$_n$GlcNAc oligosaccharide In an oven-dried flask, under a $N_2$ atmosphere, was dissolved 20 mg (0.01 mmol) of the Man$_n$GlcNAc peracetate (where n is an integer in the range from and including 5 through 8) in 1 ml of anhydrous 1,2-dichloroethane. Addition of bromotrimethylsilane Aldrich, 40 μl, 0.29 mmol), boron trifluoride etherate (Aldrich, 40 μl, 0.30 mmol) and 2,4,6-collidine (Aldrich, 45 ul, 0.3 mmol) was made via syringe. The mixture was allowed to stir at 20° C. overnight. Methylene chloride (10 ml) was added to the reaction mixture and the organic layer was washed with sat. $NaHCO_3$ solution, $H_2O$ and sat. NaCl solution. The organic layer was dried ($Na_2SO_4$) and concentrated in vacuo. The crude material was purified by flash chromatography (40:1 $CHCl_3$-MeOH) on silica gel (230–400 mesh, EM Science) to give the oligosaccharide peracetate oxazoline as a white solid (20 mg, 95%). The oligosaccharide oxazoline will be ideally characterized by its unique NMR resonance for the anomeric proton: 400 MHZ $^1H$ NMR ($CDCl_3$) ppm 5.98 (d,J=8.5 Hz) 1 H.

EXAMPLE 4

Preparation of 7S-Oligosaccharide—Bovine Serum Albumin conjugate

A. Synthesis of Activated 7S-Oligosaccharide Derivative (FIG. 3)

Figure 3:
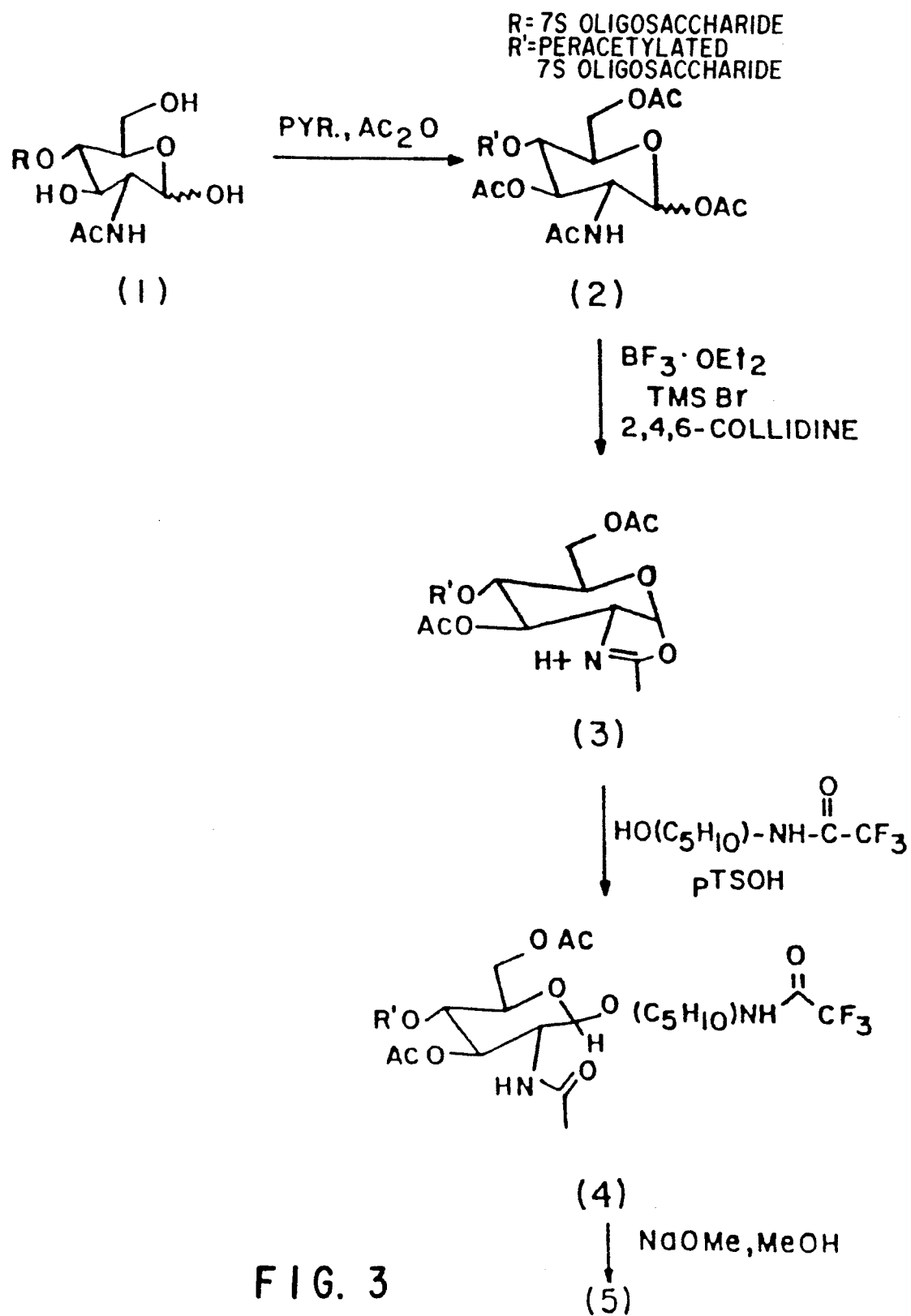
FIG. 3 is a reaction scheme showing the preparation of an oligosaccharide-protein conjugate in accordance with the invention as described in Example 4.

The 7S-oligosaccharide mixture 1 (FIG. 3), released from 7S globulin fractions of soybean meal by endonuclease H, is comprised of a mixture of high mannose type oligosaccharides with the general structure represented by Man4-9-GlcNAc (FIG. 3). The 7S-oligosaccharide mixture 1 (FIG. 3) (254 mg) is treated with acetic anhydride in pyridine, at 22°–25° C., under a nitrogen atmosphere, for 16 hrs. The 7S-oligosaccharide peracetate 2 (FIG. 3) forms a precipitate upon addition of ice. The peracetate is collected and dissolved in a minimum amount of chloroform. It is then further purified by silica gel column chromatography, (Kieselgel 60, 230–400 mesh, EM science). The column is eluted first with 2:1 (v/v) ethyl acetate/hexane to remove the excess pyridine, then with 10:1 (v/v) chloroform/methanol, to give the desired 7S-oligosaccharide-peracetate 2 as a white solid (331 mg, Rf=0.52, 10:1 v/v $CHCl_3$/MeOH).

To a solution of the 7S-oligosaccharide-peracetate 2 in 1,2-dichloroethane is added 5 to 10 molar equivalents of boron trifluoride etherate, bromotrimethylsilane and collidine. The reaction mixture is kept at 22° to 25° C., with stirring, under a nitrogen atmosphere for 16 hrs. Analysis of the reaction mixture by thin layer chromatography (10:1 chloroform/methanol, v/v) indicates the formation of a new species (Rf=0.60, 10:1 v/v $CHCl_3$/MeOH). Dichloromethane is added to the reaction mixture, which is washed with saturated aqueous sodium bicarbonate and brine; dried with anhydrous sodium sulfate and evaporated under reduced pressure to dryness. Purification by silica gel chromatography (Kieselgel 60, 230–400 mesh, EM science, eluted first with 2:1 v/v ethyl acetate/hexane, then with 40:1 v/v chloroform/methanol) affords the 7S-oligosaccharide oxazoline-peracetate 3 (FIG. 3) as a white solid (245 mg).

The oligosaccharide oxazoline-peracetate 3 so obtained is dissolved in dry 1,2-dichloroethane and treated with five to ten molar equivalents of 5-(N-trifluoroacetyl)amino-1-pentanol and p-toluenesulfonic acid. The reaction mixture is kept at ambient temperature (22°–25° C.), under a nitrogen atmosphere for 16–48 hrs. Analysis by thin layer chromatography (10:1 v/v chloroform/methanol) shows the formation of a new species 4 (FIG. 3) with lower Rf than the starting oxazoline. The reaction mixture is evaporated under reduced pressure to dryness and is used in the next step without purification.

The O-acetates and N-trifluoroacetates on the (N-trifluoroacetyl)5-aminopentyl-7S-oligosaccharide-peracetate 4 are removed by treatment with 0.2M sodium methoxide in methanol for 16 hrs at ambient temperature. At the end of the said time period, the excess methoxide is neutralized by bubbling carbon dioxide through the reaction mixture for 30 min. The methanol solvent is evaporated under reduced pressure and the resulting solid dissolved in distilled water. The aqueous solution of 5-aminopentyl-oligosaccharide 5 (FIG. 3) thus obtained is desalted using an Amicon ultrafiltration system (YCO5 membrane, molecular weight cutoff: 500). The aqueous solution retained in the ultrafiltration unit is lyophilized to a powder. The powder so obtained is further purified on a Biogel-P2 gel filtration column equilibrated with 50 mM ammonium bicarbonate solution. Fractions containing the desired 5-aminopentyl-oligosaccharide 5 are combined and lyophilized to yield a white fluffy powder (52 mg). The 400 MHZ $^1$H NMR of the white powder confirms the presence of a β-5-amino-pentyl glycoside: 4.42 ppm (d, J=8 Hz, 1H, anomeric H), 2.90 ppm (t, J=7 Hz, 2H, CH$_2$NH), 1.95 ppm (s, 3H, —NCOC$_3$), 1.57 ppm (t, J=7 Hz, 2H, —CH$_2$—CH$_2$—NH$_2$), 1.50 ppm and 1.40 ppm (m, 2H and 2H, —O—CH$_2$—CH$_2$—CH$_2$—CH$_2$—CH$_2$—NH$_2$).

To a suspension of 5-aminopentyl-7S-oligosaccharide 5 (FIG. 3) (8 mg) in dry dimethylformamide is added a solution of N-hydroxysuccinimidyl ester of bromoacetic acid (0.06M, 200 μl). The reaction is allowed to proceed at ambient temperature for 4 hrs, then kept at −10° C. for 16 hrs. The solvent is evaporated on a nitrogen evaporator. The N-bromoacetyl-5-aminopentyl-7S-oligosaccharide 6 (FIG. 3) is precipitated by the addition of acetone. The precipitate is washed twice with acetone and the solvent removed by centrifugation. The white precipitate isolated is further purified over a Biogel P2 gel filtration column equilibrated with distilled water. All fractions containing carbohydrates are combined and lyophilized to give 5.0 mg of a white powder. $^1$H NMR (400 MHz) shows a downfield shift of 0.25 ppm for the methylene group next to the amine, confirming that the pendant amino group has been bromoacetylated: 4.42 ppm (d, J=8 Hz, anomeric H), 3.15 ppm (m, CH$_2$NHC(O)CH$_2$Br), 1.97 ppm (s, NHC(O)CH$_3$), 1.36 and 1.4-1.6 ppm (m, 6H total, —O—CH$_2$—CH$_2$CH$_2$—CH$_2$—CH$_2$—NH).

B. Conjugation of Activated 7S-Oligosaccharide Derivative with Bovine Serum Albumin (BSA)

The 7S-oligosaccharide was covalently attached to an exposed, accessible cysteine on the protein, namely Cys-34 of bovine serum albumin. To the N-bromoacetyl-5-aminopentyl-7S-oligosaccharide derivative obtained as described above is added a solution containing 0.5 mg/ml of bovine serum albumin in 0.05M sodium phosphate, 1 mM EDTA, 1% glycerol, pH 7.5. The molar ratio of the activated oligosaccharide derivative to the protein is preferred to be 20:1 or greater. The mixture so obtained is kept in the dark, under a nitrogen atmosphere for 16 hrs. At the end of the said time period, the mixture is dialyzed against several changes of water.

C. Analysis of the 7S-Oligosaccharide—BSA Conjugate

The reaction mixture so obtained was analyzed by SDS-polyacrylamide gel electrophoresis. Concanavalin A lectin blot of the gel shows high mannose oligosaccharide associated only with new oligosaccharide-protein conjugate.

D. Purification of the 7S-Oligosaccharide—BSA Conjugate

An aliquot of the reaction mixture (823 μg of BSA) was dialyzed exhaustively into 0.01M sodium phosphate and 0.5M sodium chloride, pH 6.8. The dialysate was passed slowly through a Concanavalin A lectin column (0.5 ml) equilibrated with 0.01M sodium phosphate, 0.5M sodium chloride, 1 mM MgCl$_2$, 1 mM MnCl$_2$, and 1 mM CaCl$_2$, pH 6.8. Fractions containing unreacted BSA, which did not bind to the lectin column, were assayed by the Bradford assay and pooled (371 μg). The 7S-oligosaccharide-BSA conjugate, which bound to the lectin column, was eluted with 0.01M sodium phosphate, 0.5M sodium chloride, 0.5M methyl mannoside, pH 6.8. Fractions collected were assayed according to Bradford and fractions containing the neoglycoprotein were combined (113 μg).

EXAMPLE 5

A. Preparation of 7S-Oligosaccharide-γ-Interferon Conjugate

This example describes the covalent attachment of 7S-oligosaccharide to a cysteine on murine-γ-interferon. This cysteine is exposed by reductive cleavage of an intermolecular disulfide bridge. The murine γ-interferon is obtained from Genentech Co., California. To 1 mg (0.07 umol) of γ-interferon in 1 ml of 0.1M sodium phosphate, 0.5M sodium chloride pH 7.8 is added β-mercaptoethanol (12 μl, 0.17 mmole). The mixture so obtained is incubated at ambient temperature (22°-25° C.), in the absence of light, under a nitrogen atmosphere for 3 hr. The reduced murine γ-interferon is purified on a Biogel-P6 column equilibrated with 0.05M sodium phosphate, 1 mM EDTA, 5% glycerol pH 6.8. The protein, eluted in the void volume, is added to bromoacetylated-5-aminopentyl-7S-oligosaccharide derivative (2.4 mg, 1.5 μmol). The mixture so obtained is incubated at ambient temperature (22°-25° C.), in the absence of light, under a nitrogen atmosphere for 16 hr.

B. Analysis of the Reaction Mixture of γ-Interferon and Activated 7S-oligosaccharide Derivative Analysis of the reaction mixture so obtained by SDS-PAGE shows the formation of a new protein species which is approximately 2 kDa larger than native γ-interferon. Concanavalin A lectin blot also shows the presence of high mannose oligosaccharide associated with this new protein species.

C. Purification of 7S-oligosaccharide-γ-Interferon Conjugate

The excess bromoacetylated-5-aminopentyl-7S-oligosaccharide derivative is removed from the reaction mixture by passing it through a Biogel-P6 gel filtration column equilibrated with Concanavalin A buffer (0.5M sodium chloride, 0.01M sodium phosphate, 1 mM calcium (II) chloride, 1 mM magnesium (II) chloride, 1 mM manganese (II) chloride pH 6.8). The mixture of modified and unmodified γ-interferon thus obtained is adsorbed on a concanavalin A lectin column. The unmodified γ-interferon is eluted in the void volume whereas the modified γ-interferon is eluted by 0.5 M methyl mannoside in Con A buffer. The protein concentrations are estimated using Bradford assay.

EXAMPLE 6

A. Preparation of 7S-Oligosaccharide—Granulocyte—Colony—Stimulating Factor Conjugate This example describes the covalent attachment of 7S-oligosaccharide to an inaccessible cysteine on protein, for example, Cys-17 of granulocyte-colony stimulating factor. Recombinant granulocyte-colony stimulating factor(rG-CSF), isolated from Chinese hamster ovary cells, is obtained from Chugai Pharmaceutical Co., Japan. A solution of rG-CSF (13 nmole/ml, 250 µg/ml) in 4 ml of 0.01M sodium phosphate, 0.1M sodium chloride, pH 7.9 is added under a nitrogen atmosphere to a twenty-five fold molar excess of N-bromoacetyl-5-aminopentyl-7S-oligosaccharide. Solid urea is added to this mixture so that the final concentration of the denaturant is 6M. The reaction is allowed to proceed in the dark, at ambient temperature (22°–25° C.) for 1.5 hrs. The reaction mixture so obtained is dialyzed against 0.01M sodium phosphate, 0.1M sodium chloride, 3M urea, pH 7.6 so as to renature the protein.

B. Analysis of 7S-Oligosaccharide—Recombinant Granulocyte—Colony stimulating Factor Conjugate SDS-Gel electrophoresis of the reaction mixture by non-reducing, 10 to 20% polyacrylamide gel indicates the formation of a new protein species with a molecular weight which is approximately 2 kDa larger than the native rG-CSF. A concanavalin A lectin blot verifies that high mannose oligosaccharide is only associated with this new protein species. Analysis of the reaction mixture by reverse-phase HPLC (Waters deltapak, 5µ particle size, 300 Å pore size, 3.9 mm×150 mm, linear gradient of 37% to 43% isopropanol in 0.025M sodium phosphate, pH 6.5, flow rate 1 ml/min.) also shows that 34% of the rG-CSF has been labelled with the N-bromoacetyl-5-aminopentyl-7S-oligosaccharide derivative.

C. Purification of 7S-Oligosaccharide-G-CSF Conjugate.

Purification of the 7S-oligosaccharide-G-CSF conjugate is effected by using reverse-phase HPLC. The dialysate is injected onto a C18 column (Waters deltapak, 5µ particle size, 300 Å pore size, 3.9 mm×150 mm), equilibrated with a buffer consisting of 37:63 isopropanol (IPA)/0.025 M sodium phosphate, pH 6.5. The glycoprotein conjugate is separated from the unmodified protein using a linear gradient of 37% IPA to 43% IPA (flow rate 1 ml/min) as the eluant. The glycoprotein conjugate has a shorter retention time than the unmodified protein.

What is claimed is:

1. A process for the production of a peracetyl saccharide oxazoline comprising reacting a peracetyl saccharide having a reducing terminus with a 2-N-acetyl group, with reagents consisting essentially of boron trifluoride etherate and a compound selected from the group consisting of bromotrimethylsilane, chlorotrimethylsilane and iodotrimethylsilane.

2. A method for the production of a peracetyl oxazoline according to claim 1, wherein the peracetyl saccharide is selected from mono-, di-, and oligosaccharides.

3. A method for the production of an oxazoline according to claim 1, wherein the saccharide may be a pertrichloroacetyl, pertrifluoroacetyl or perbenzoylacetyl saccharide.

4. A method for the production of a peracetyl oxazoline according to claim 1, wherein the reagents are composed of a 1:1 mixture of boron trifluoride etherate and the compound.

5. A method for the production of a peracetyl oxazoline according to claim 1, wherein an acid scavenger is added which is selected from the group of acid scavengers consisting of 2,4,6-collidine, pyridine, triethylamine, dimethylaminopyridine and N,N-diisopropylethylamine.

6. A process for the production of a peracetyl saccharide oxazoline comprising reacting a peracetyl saccharide having a reducing terminus and a 2-N-acetyl group, with reagents consisting essentially of boron trifluoride etherate and a compound selected from the group consisting of bromotrimethylsilane and chlorodimethylsilane.

* * * * *

UNITED STATES PATENT AND TRADEMARK OFFICE
CERTIFICATE OF CORRECTION

PATENT NO. : 5,241,072
DATED : August 31, 1993
INVENTOR(S) : Colon and Davis

It is certified that error appears in the above-indentified patent and that said Letters Patent is hereby corrected as shown below:

On the Title Page, Item [75], should read Marcelo Colon, Gurabo, P.R.; Jeffrey T. Davis, Watertown, Mass.

Signed and Sealed this

Twenty-first Day of June, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,241,072

DATED : August 31, 1993

INVENTOR(S) : Marcelo Colon, Jeffrey T. Davis, James R. Rasmussen, Marianne Borowski, Barbara Y. Wan, and Shirish Hirani It is certified that error appears in the above-identified patent and that said Letters Patent is hereby corrected as shown below: Title page:

In the Assignee section, change "Genzyne Corporation" to --Genzyme Corporation--

Please add --Attorney: Bromberg & Sunstein-- before the abstract.

Signed and Sealed this

First Day of July, 1997

*Attest:*

BRUCE LEHMAN

*Attesting Officer*     *Commissioner of Patents and Trademarks*